US00PP09656P

United States Patent [19]

Moore

[11] Patent Number: Plant 9,656

[45] Date of Patent: Oct. 15, 1996

[54] MINIATURE ROSE PLANT NAMED 'MOR BROWN'

[76] Inventor: Ralph S. Moore, 2519 E. Noble Ave., Visalia, Calif. 93292

[21] Appl. No.: 375,542

[22] Filed: Jan. 19, 1995

[51] Int. Cl.[6] ..... A01H 5/00

[52] U.S. Cl. ..... Plt./10.1

[58] Field of Search ..... Plt./7.1, 10.1

*Primary Examiner*—Howard J. Locker

[57] ABSTRACT

This invention relates to a new and distinct cultivar of miniature rose, primarily identified by the apricot color of its petals and double flowers.

1 Drawing Sheet

The present invention relates to a new and distinct culvitar of hardy, dwarf, bush type rose plant of the miniature class. The cultivar is primarily charcterized as to novelty by its apricot color and double flowers.

The cultivar is further characterized by:

An abundance of blooms, with flowers usually borne singly to the stem.

Slight Fragrance.

A plant of vigorous, rounded to upright growth shape, with semi-glossy to matte foliage with pointed leaflets; the buds and flowers being similar in form to 'MORyou' ('Just For You', miniature rose; U.S. Plant Pat. No. 8,200) but differing in color, being apricot instead of pink.

A plant which grows and blooms satisfactorily both in greenhouse and outdoors; with repeat bloom, is good for growing in pots, and provides excellent garden decoration as well as cut flowers.

The present cultivar of miniature rose was originated by me at my nursery, located at Visalia, Calif., under conditions, of careful control and observation, as a result of a cross between 'MORseqold' ('Sequoia Gold', miniature rose; U.S. Plant Pat. No. 6,617) as the seed parent and 'Golden Angel' (U.S. Plant Pat. No. 4,028) as the pollen parent.

Subsequent to my origination of the cultivar I successfully asexually reproduced this new cultivar at my nursery, located as aforementioned, by budding as well as by cuttings; the reproductions have run true in all respects.

The photograph illustrates the cultivar including the foliage, buds and flowers (stamens not shown).

Plant part coloration illustrated is as true as reasonably possible to attain in photographic illustrations of this type.

Referring now specifically to the new and distinct cultivar of miniature rose plant, the following is a detailed description thereof in outline; all major color plant identification by reference to the R.H.S. Colour Chart (Royal Horticultural Society) except where common terms of color definition are employed.

Type: Hardy; dwarf; upright; seeding; greenhouse; outdoors; cut flowers; garden decoration; potted plant.

Class: Miniature.

*Cultivar identification.*—MORbrown'.

*(Commercial synonym.*—Apricot Twist).

Flowers borne: Usually singly, or occasionally in loose clusters, on sturdy, wiry stems.

Quantity of bloom: Abundant outside and inside greenhouse.

Bud:

*Peduncle.*—Medium length; slender but sturdy; erect; medium green, near Green Group 138B, sometimes tinted bronze (outdoors); nearly smooth.

*Before calyx breaks.*—Size—small.

*Form.*—Pointed, with several small foliaceous appendages on surface of the bud; with foliaceous parts extending beyond the tip of the bud equal to one half or less than one half of its length.

*Color.*—Medium green, near Green Group 138A, occasionally tinted with bronze (outdoors).

*As calyx breaks.*—Color— apricot, near Orange Group 24B and Orange 25B.

*Opening.*—Opens well in all weather.

Bloom:

*Size when fully open.*—Small, averaging about 40 mm or 1¾".

*Petalage.*—Double— averaging about 40 petals, arranged regularly plus several small petaloids.

*Form.*—Full, high centered at first, becoming rounded with petals rolled loosely outward and downward. Fully opened flowers usually show stamens (not shown in photo).

*Sepals.*—Permanent; spear shaped; recurved.

*Behavior.*—Opens well in all weather; spent petals or flowers drop off.

*Flower longevity (July and August* 1995).—Plant in pot—4 to 6 days or longer. Cut flowers at living room temperature—4 to 5 days.

Petals: Fairly thick; satiny on inside and on outside surface.

*Shape.*—Outside petals: broad lanceolate (wedge shaped) with small acute tip. Intermediate: broad lanceolate with nearly round or short acute tip. Inside: lanceolate with acute tip.

*Color.*—(Newly opening flower from plant grown in plastic greenhouse in October, 1994, Visalia, Calif. (Photograph taken Oct. 1994)). Outside petal: Outside surface— orange (apricot) near Orange Group 26C. Inside surface— near Orange Group 26C blending into yellow at petal base. Intermediate petal: Outside surface similar to outside petal; Inside surface similar to outside petal. Inner petal: Outside surface similar to intermediate petal. Inside surface similar to intermediate petal. General color effect: newly opened flowers— apricot. 3 days open—color similar to newly opened flower, but lighter and less bright. Flower(petal) color becomes progressively lighter as the flowers age.

Reproductive organs:

*Stamens.*—Moderately abundant, arranged regularly about the pistol.

*Filaments.*—Fairly short, yellow.

*Anthers.*—Well formed, yellow.

*Pollen.*—Moderate.

*Pistils.*—Average number.

*Styles.*—Long; yellowish; bunched.

*Ovaries.*—All enclosed in calyx.

*Hips.*—Usually none.

*Seed.*—None

Foliage:

*Leaves.*—Compound of five (sometimes 3 or 7) leaflets; medium small); leathery; matte.

*Leaflets.*—Shape: Broad lanceolate; apex acute; base—rounded. Color: Medium green (can be as dark as Green 137A but usually lighter green); new growth— normal (medium) green sometimes tinted reddish. Rachis: Medium strength; upper side smooth; grooved; underside may have several small thorns (or claws). Stipules: Medium to short length; medium width; medium to short length narrow points which turn out usually at about 45° or less. Color similar to leaflets.

*Habit.*—Dwarf; bush; upright; much branched. Plant height: 45–50 cm. Plant spread: 45 cm.

*Growth.*—Vigorous; internodes short.

*Canes.*—Medium slender; sturdy.

*Main stems.*—Color: Medium green, near Green Group 134B.

*Thorns.*—Average of varying size and length, usually straight to slightly downward, color: brown to gray. Hairs— few or none.

The miniature rose plant and its flowers as heretofore described may vary in slight detail due to climate, soil and cultural conditions under which the cultivar may be grown; the present description being of the cultivar as grown at Visalia, Calif.

The following is claimed:

1. A new and distinct cultivar of rose plant of the miniature class, of hardy, dwarf, bushy, much branched habit substantially as illustrated and described, characterized by buds and flowers, basically apricot, the bud being pointed in the early stage, resembling in form 'MORyou' (miniature), with the open flower being double and rounded with 40 or more petals; and further characterized by a plant of compact, vigorous, upright shape with main stems and shoots of average thorniness, the said plant being easy to propagate from soft-wood cuttings with an abundance of small, matte foliage, the flowers being usually borne singly on medium length stems.

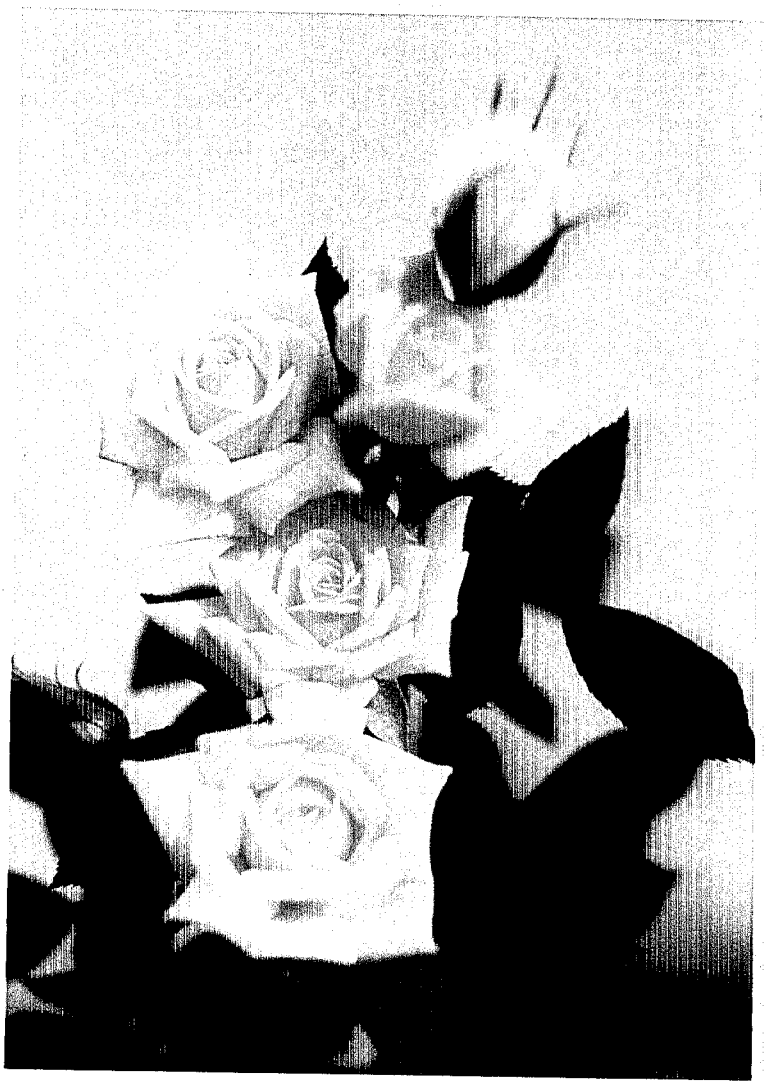

* * * * *